(12) United States Patent
Yamauchi

(10) Patent No.: US 7,038,778 B2
(45) Date of Patent: May 2, 2006

(54) SPECTROMETER AND SPECTRALLY SEPARATING METHOD

(75) Inventor: Kazunori Yamauchi, Hamamatsu (JP)

(73) Assignee: Hamamatsu Photonics K.K., Shizuoka (JP)

(*) Notice: Subject to any disclaimer, the term of this patent is extended or adjusted under 35 U.S.C. 154(b) by 95 days.

(21) Appl. No.: 10/470,380

(22) PCT Filed: Aug. 13, 2002

(86) PCT No.: PCT/JP02/08260

§ 371 (c)(1),
(2), (4) Date: Jul. 28, 2003

(87) PCT Pub. No.: WO03/016842

PCT Pub. Date: Feb. 27, 2003

(65) Prior Publication Data

US 2004/0070765 A1    Apr. 15, 2004

(30) Foreign Application Priority Data

Aug. 13, 2001 (JP) .............................. 2001-245590

(51) Int. Cl.
*G01N 21/25* (2006.01)
(52) U.S. Cl. ...................... 356/419; 356/416; 250/226
(58) Field of Classification Search ................ 356/419, 356/409, 414, 417, 418, 432, 451, 452
See application file for complete search history.

(56) References Cited

U.S. PATENT DOCUMENTS

| | | | |
|---|---|---|---|
| 4,244,045 A | 1/1981 | Nosu et al. ..................... 370/3 |
| 5,995,235 A | 11/1999 | Sui et al. ..................... 356/419 |
| 6,243,175 B1 | 6/2001 | Pelekhaty ................... 359/119 |
| 6,249,348 B1 * | 6/2001 | Jung et al. ................... 356/419 |
| 6,362,888 B1 * | 3/2002 | Jung et al. ................... 356/419 |
| 6,683,314 B1 | 1/2004 | Oostman, Jr. et al. ... 250/461.2 |

FOREIGN PATENT DOCUMENTS

| | | | |
|---|---|---|---|
| DE | 196 04 167 | | 8/1997 |
| EP | 0 421 304 | | 4/1991 |
| JP | 57 106843 | | 7/1982 |
| JP | 59-131124 | | 7/1984 |
| JP | 59-170734 | * | 9/1984 |
| JP | 60-026008 | | 2/1985 |
| JP | 26008/1985 | * | 2/1985 |
| JP | 61 205906 | | 9/1986 |
| JP | 03-205521 | * | 9/1991 |
| JP | 10-062246 | * | 3/1998 |
| JP | 11-006766 | | 1/1999 |
| JP | 2000-111406 | * | 4/2000 |
| JP | 2001-201655 | | 7/2001 |
| WO | WO 01/46659 | | 6/2001 |

* cited by examiner

*Primary Examiner*—Gregory J. Toatley, Jr.
*Assistant Examiner*—Roy M. Punnoose
(74) *Attorney, Agent, or Firm*—Drinker Biddle & Reath LLP

(57) ABSTRACT

A light from a light source is transmitted through a sample cell and is made incident into a spectroscopic portion. The spectroscopic portion comprises interference filters which transmit light components different in wavelengths and photodiodes corresponding to the respective interference filters. Dielectric films to compose an interference filter have relatively satisfactory features to reflect a light component of wavelengths other than a light component of a wavelength to be transmitted. At each interference filter, an incident light is split into a light component to be transmitted and a light component to be reflected. By making the reflected light component into an incident light into a following-order interference filter, light components of nine wavelength types are detected.

18 Claims, 13 Drawing Sheets

SPECTROMETER AND SPECTRALLY SEPARATING METHOD

TECHNICAL FIELD

This invention relates to a spectroscopic instrument and a spectroscopic method to be used in, for example, a blood test.

BACKGROUND ART

A spectroscopic instrument is an instrument for measuring absorbency of a testing sample by irradiating light from a light source onto the test sample and changing intensity of the light transmitted through or reflected from the test sample to an electric signal, and has been applied to various fields. When a spectroscopic instrument is applied to, for example, a color measurement or a blood test, out of light transmitted through a test sample, absorbency of a plurality of light components different in wavelengths, namely, each of the multiple wavelengths is measured. Such spectroscopic instruments include a rotary plate-system spectroscopic instrument as disclosed in Japanese Unexamined Patent Publication No. Sho-59-131124, for example. In this spectroscopic instrument, by mechanically rotating a rotary plate so that a filter which transmits a light component of a wavelength to be detected is located in an optical path, detection of multiple wavelengths is enabled.

However, since the rotary plate-system spectroscopic instrument selects a filter by mechanically rotating the rotary plate, it takes time to detect multiple wavelengths. Although a quick examination of multiple samples and multiple items is demanded in a blood test, the rotary plate-system instrument cannot satisfy this demand.

Instruments to satisfy this demand include half mirror-system spectroscopic instruments as disclosed in Japanese Unexamined Patent Publication No. Hei-11-6766 and Japanese Unexamined Patent Publication No. Sho-59-170734, for example. These spectroscopic instruments have a structure to detect multiple wavelengths by a plurality of half mirrors and a plurality of light-receiving elements. The half mirror-system spectroscopic instrument detects multiple wavelengths by splitting, at respective half mirrors, an incident light into a transmitted light and a reflected light and using the transmitted light as an incident light of a half mirror positioned in the next order. Therefore, compared to the above-described rotary plate-system spectroscopic instrument that detects multiple wavelengths by mechanically selecting a wavelength, multiple wavelengths can be speedily detected.

SUMMARY OF THE INVENTION

However, according to a half mirror-system spectroscopic instrument, a light flux is split into one second by each half mirror. Accordingly, the S/N ratio declines at light-receiving elements positioned in the latter orders since an incident light weakens considerably, whereby detecting efficiency, which is a light component detecting sensitivity, is deteriorated. For example, if eight half mirrors are provided to detect nine wavelength types, light intensity of light transmitted through the eighth half mirror becomes $(1/2)^8 = 1/256$ compared to the initial intensity, and detecting efficiency of a light component of that wavelength is considerably deteriorated. In order to cope therewith, the amount of light from the light source must be increased, however, this results in an increase in power consumption.

The present invention has been made to solve such conventional problems and to provide a spectroscopic instrument and a spectroscopic method which can detect a plurality of light components different in wavelengths at a high detecting efficiency and at a high speed.

A spectroscopic instrument according to the present invention is a spectroscopic instrument for detecting a plurality of light components different in wavelengths, comprising: a plurality of interference filters which are respectively different in wavelengths of light components to be transmitted therethrough and to which a light from a light source is transmitted in order; and a plurality of photodetecting means corresponding to each of the plurality of interference filters, for detecting a light component transmitted through the corresponding interference filter, wherein each of the plurality of interference filters splits an incident light into a light component to be reflected and a light component to be transmitted and makes the reflected light component into an incident light into an interference filter positioned in the next order, whereby the light from the light source is transmitted to the plurality of interference filters in order.

According to the spectroscopic instrument of the present invention, the plurality of interference filters split the irrespective incident lights in to a light component to be reflected and a light component to be transmitted and make the reflected light component into an incident light into an interference filter positioned in the next order, whereby a light from the light source is transmitted to the plurality of interference filters in order, and light components transmitted through the respective interference filters are detected by the respective photo detecting means, where by multiple wavelengths are detected. An interference filter is composed of dielectric layers (dielectric multilayered films), and a light component of a predetermined wavelength is transmitted by an interference effect of the dielectric layers. According to the present inventor, it has been discovered that these dielectric layers have relatively satisfactory features to reflect a light component of wavelengths other than a light component of a wavelength transmitted through the interference filter. Accordingly, since an incident light of a relatively high intensity is made incident into interference filters positioned in the latter orders, as well, the detecting efficiency can be improved.

In addition, according to the spectroscopic instrument of the present invention, an incident light into each interference filter is split into a light component to be transmitted and a light component to be reflected, and the reflected light component is made into an incident light into an interference filter positioned in the next order. Since the spectroscopic instrument according to the present invention detects multiple wavelengths by not mechanically but optically selecting a wavelength, high-speed detection of multiple wavelengths becomes possible.

A spectroscopic method according to the present invention is a spectroscopic method for detecting a plurality of light components different in wavelengths, wherein at each of a plurality of interference filters respectively different in wavelengths of light components to be transmitted therethrough, an incident light into each interference filter is split into a light component to be reflected and a light component to be transmitted and the reflected light component is made into an incident light into an interference filter positioned in the next order, whereby a light from a light source is transmitted to the plurality of interference filters in order so as to detect light components transmitted through the respective interference filters.

According to the spectroscopic method of the present invention, for reasons similar to those of the spectroscopic instruments according to the present invention, it becomes possible to detect a plurality of light components different in wavelengths at a high detecting efficiency and at a high speed.

Moreover, a spectroscopic instrument according to the present invention comprises: a plurality of photodetectors arranged so that the light is made incident in time series at the speed of light, and is characterized in that the photodetectors each have a photoelectric transducer and an interference filter fixed to the light incident side of the photoelectric transducer, a transmitting wavelength and a reflecting wavelength band of the respective interference filters are different, and a transmitting wavelength of the interference filter of a latter order is included in a reflecting wavelength band of the interference filter of a former order. Irrespective of the transmitting wavelength of the interference filter, a total reflection mirror having an aperture may be provided on the light incident surface side thereof.

In addition, if the plurality of photodetectors are arranged in a circle, an air flow-in path into the inside of the circle becomes narrow, therefore, an output fluctuation of the photodetectors caused by air undulations can be suppressed.

In addition, if an infrared cut filter is arranged on the near side of the photodetectors, generation of noise caused by infrared light can be suppressed, and if the inner surface of a cylindrical body to compose a photodetector is black, noise caused by an internal reflection of the cylindrical body can be suppressed.

BEST MODE FOR CARRYING OUT THE INVENTION

A spectroscopic instrument according to a preferred embodiment of the present invention will be described by use of drawings.

Figure 1:
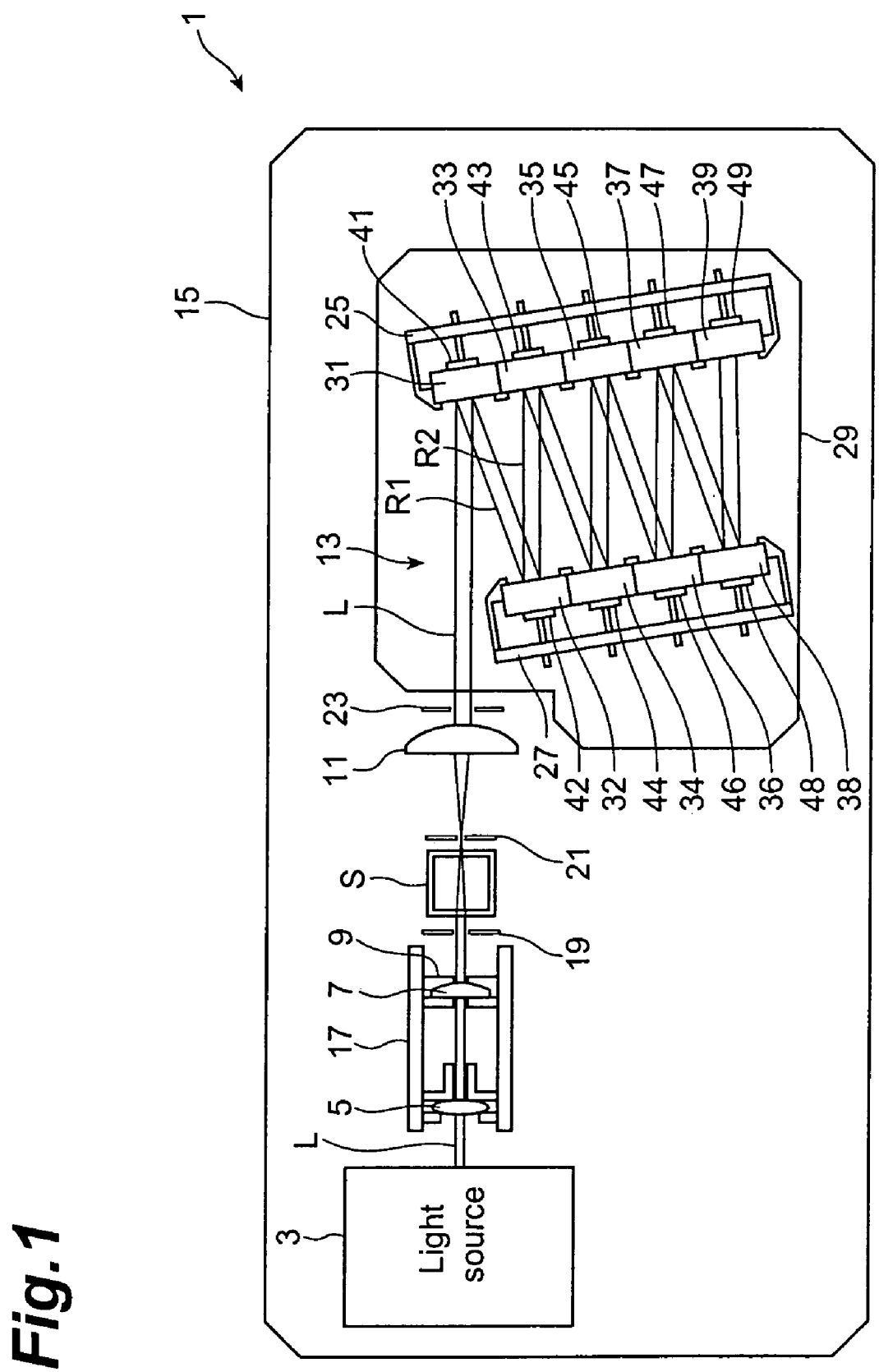
FIG. 1 is a schematic view of a spectroscopic instrument according to the first embodiment of the present invention.

FIG. 1 is a schematic view of a spectroscopic instrument according to a first embodiment of the present invention. A spectroscopic instrument 1 is for detecting light components of nine wavelength types, which comprises: a light source 3 including, for example, a 20W-iodide bulb, two lenses 5 and 7 for condensing light L emitted from the light source 3; an aperture 9 through which light L transmitted through the lenses 5 and 7 passes; a lens 11 for making light L transmitted through the aperture 9 and transmitted through a sample cell S in which a test sample (for example, blood) is contained into parallel light rays; and a spectroscopic portion 13 into which light L made into parallel light rays by the lens 11 is made incident. These components to construct the spectroscopic instrument 1 are housed in a casing (cylindrical body) 15.

The lens 5, lens 7, and aperture 9 are held by a holding portion 17, and the lens 5, the lens 7, and the aperture 9 are arranged in order along the optical path of the light L. Section dimensions of light L when the light L is made incident into the sample cell S are defined by the lens 5, lens 7, and aperture 9. This section is a section located at a 90 degree-angle with respect to the traveling direction of the light L, and the dimensions are 3 mm long×3 mm wide, for example.

An arrangement place of the sample cell S exists in an optical path between the aperture 9 and lens 11. In a manner sandwiching this arrangement place, slits 19 and 21 are arranged. In addition, a slit 23 is located in an optical path between the lens 11 and spectroscopic portion 13.

Now, a structure of the spectroscopic portion 13 will be described in detail. The spectroscopic portion 13 comprises: nine interference filters 31–39; and nine photodiodes 41–49 which correspond to the respective interference filters 31–39 and detect light components transmitted through the corresponding interference filters 31–39. The photodiodes 41–49 are examples of photodetecting means. Photodiodes which can be used in the present embodiment include a Si photodiode, for example.

The interference filters 31, 33, 35, 37, and 39 are arranged so that their respective incident surfaces are lined in one direction, and in this condition, the interference filters are held by a holding portion 25. The holding portion 25 is arranged so that a light L made incident into the spectroscopic portion 13 is made incident into the interference filter 31 at an appointed angle. To respective emitting surfaces of the interference filters 31, 33, 35, 37, and 39, the photodiodes 41, 43, 45, 47, and 49 are attached. Thus, the respective photodiodes detect light components transmitted through the corresponding interference filters.

Similarly, the interference filters 32, 34, 36, and 38 are also arranged so that their respective incident surfaces are lined in one direction, and in this condition, the interference filters are held by a holding portion 27. The holding portion 27 is arranged at a position not to intersect an optical path of light L after being made incident into the spectroscopic portion 13 before being made incident into the interference filter 31 so that the interference filters held by the holding portion 27 are opposed to the interference filters held by the holding portion 25. To respective emitting surfaces of the interference filters 32, 34, 36, and 38, the photodiodes 42, 44, 46, and 48 are attached. Thus, the respective photodiodes detect light components transmitted through the corresponding interference filters. In the spectroscopic portion 13, provided is an electronic circuit (unillustrated) such as an amplifier for amplifying the light components detected by the respective photodiodes 41–49. These components to construct the spectroscopic portion 13 are housed in a casing (cylindrical body) 29.

The interference filters 31–39 split respective incident lights into a light component to be reflected and a light component to be transmitted. By arranging the holding portions 25 and 27 as in the above, a reflected light component becomes an incident light into an interference filter positioned in the next order, whereby light L from the light source 3 is transmitted in numerical order of the interference filters 31–39. The interference filters 31–39 have functions as band-pass filters, and light components of wavelengths which the respective filters transmit are shown in Table 1.

TABLE 1

| Interference filter 31 | 340 nm |
| Interference filter 32 | 415 nm |
| Interference filter 33 | 450 nm |
| Interference filter 34 | 510 nm |
| Interference filter 35 | 540 nm |
| Interference filter 36 | 568 nm |
| Interference filter 37 | 600 nm |
| Interference filter 38 | 690 nm |
| Interference filter 39 | 800 nm |

Figure 2:
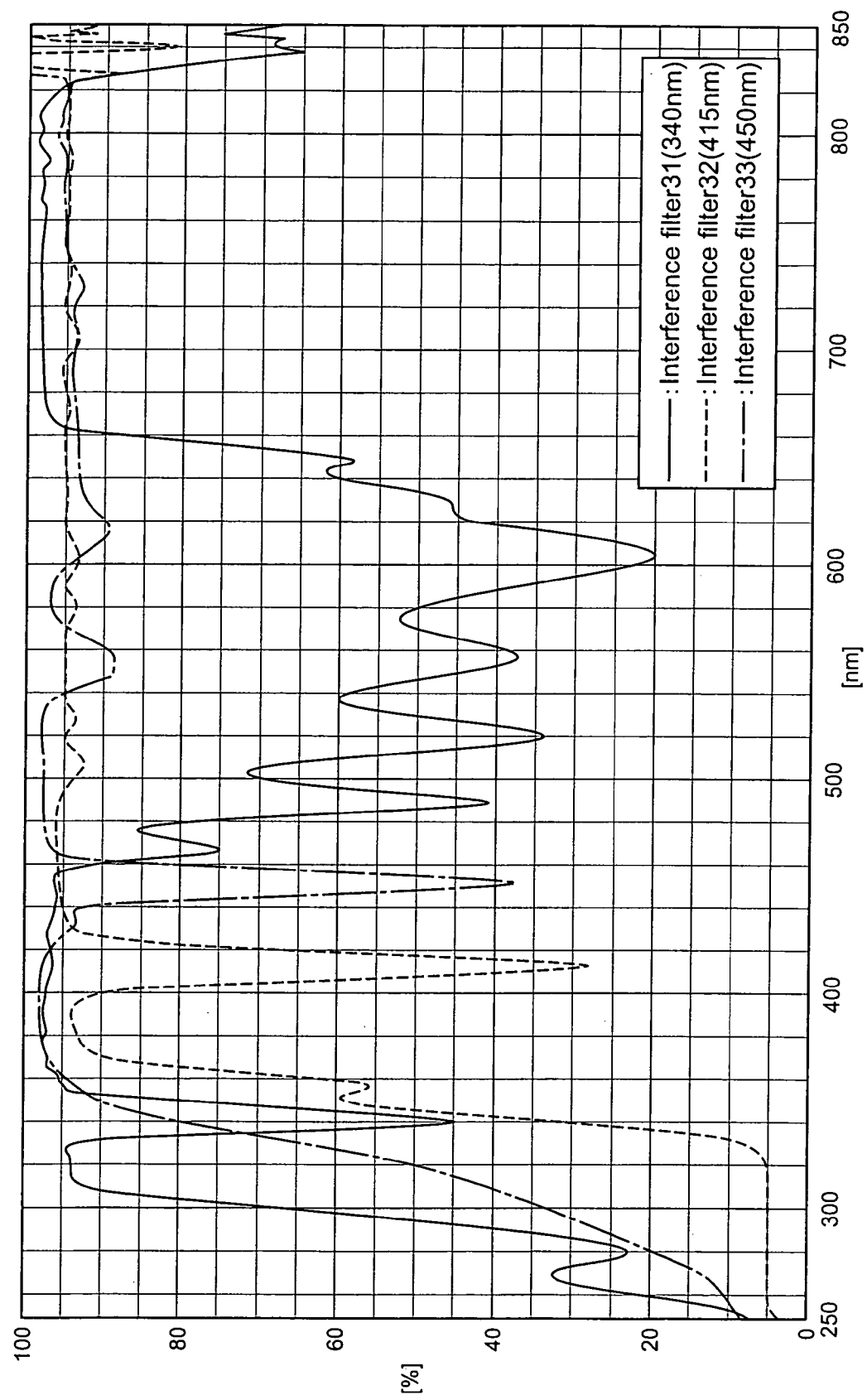
FIG. 2 is a diagram indicating a graph showing a relationship between the wavelength and reflectance of an interference filter (transmission wavelength: 340 nm, 415 nm, 450 nm) provided in the first embodiment.
Figure 3:
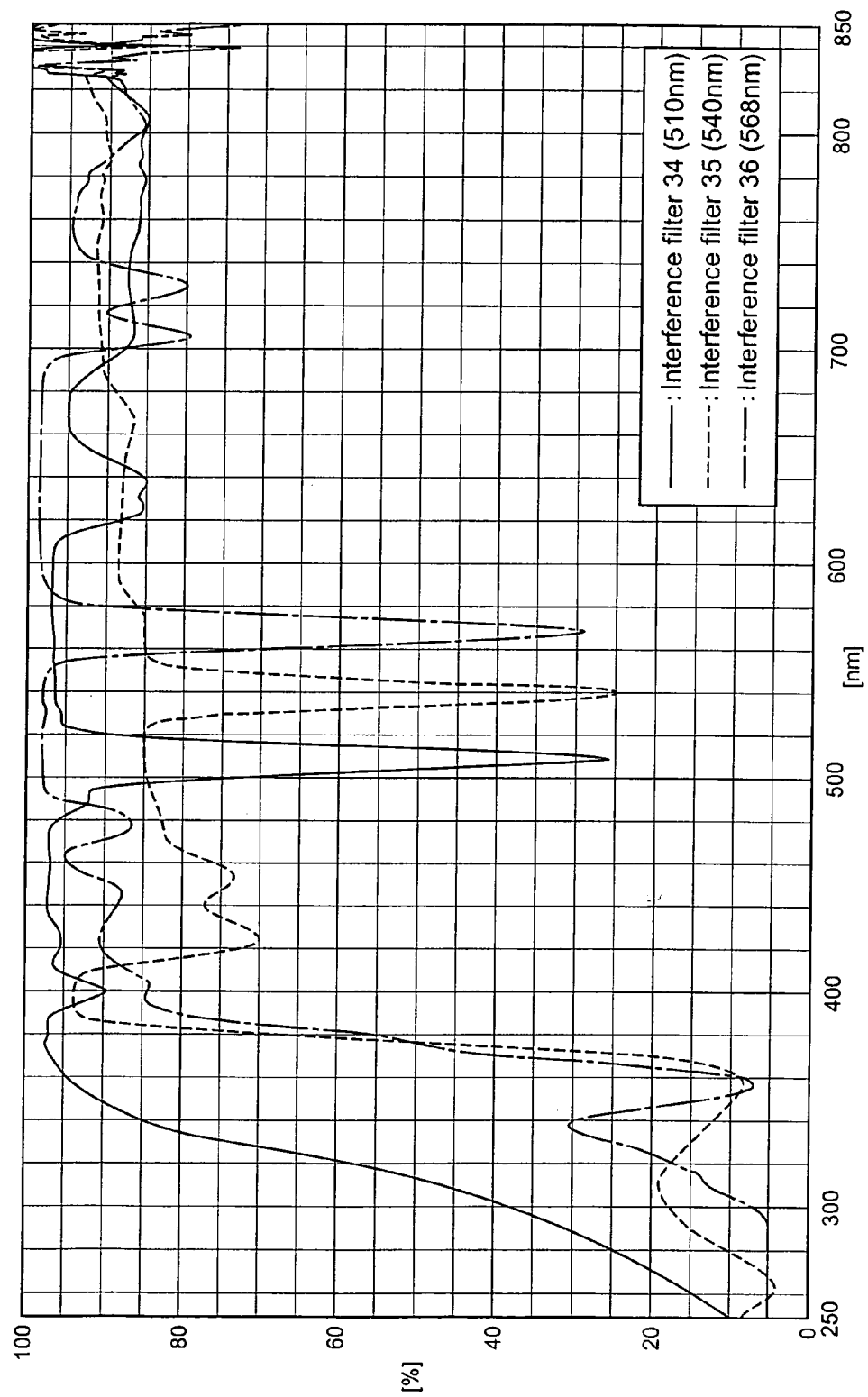
FIG. 3 is a diagram indicating a graph showing a relationship between the wavelength and reflectance of an interference filter (transmission wavelength: 510 nm, 540 nm, 568 nm) provided in the first embodiment.
Figure 4:
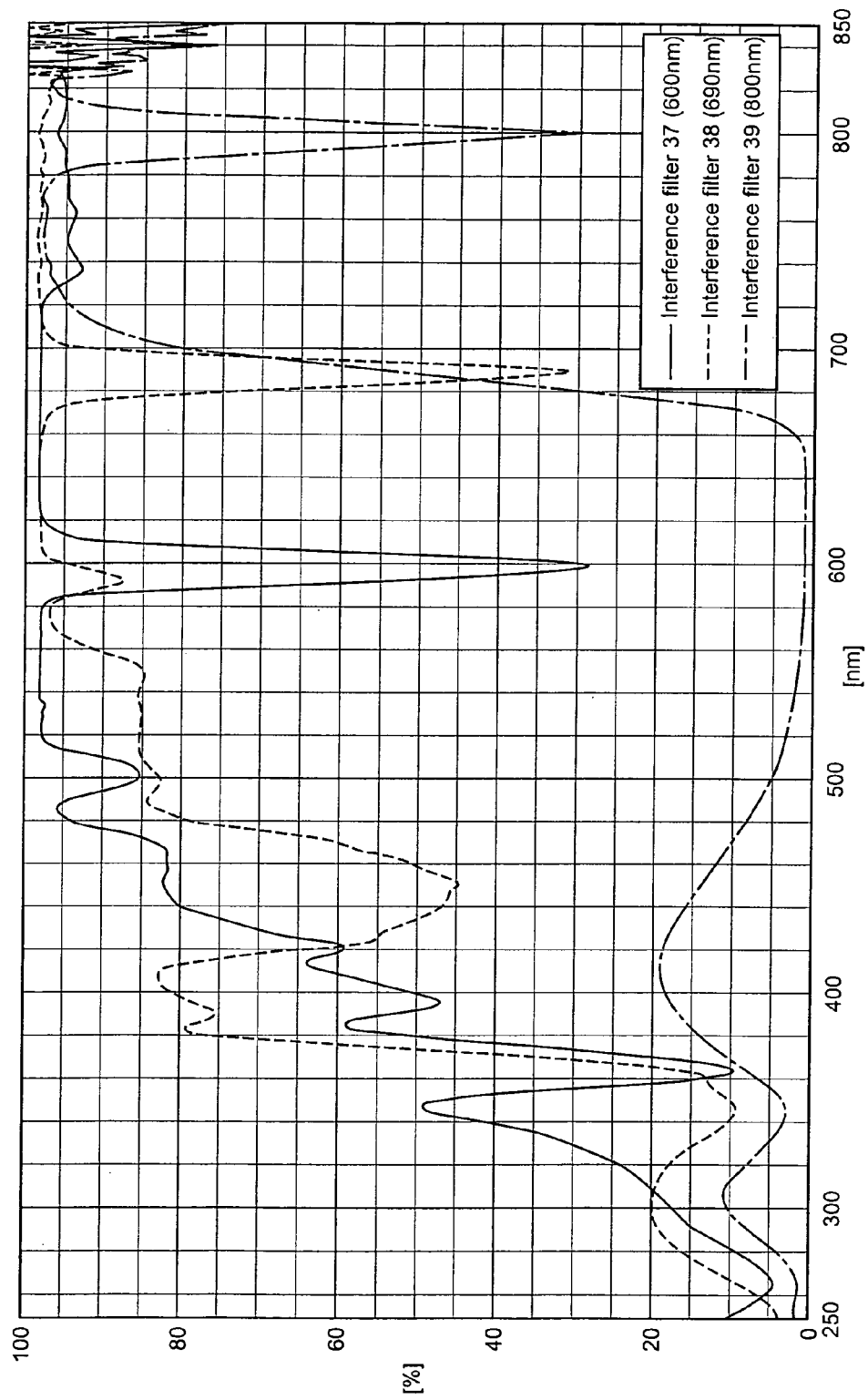
FIG. 4 is a diagram indicating a graph showing a relationship between the wavelength and reflectance of an interference filter (transmission wavelength: 600 nm, 690 nm, 800 nm) provided in the first embodiment.

Herein, an interference filter is an optical filter which is provided by layering multiple thin films having an appointed optical thickness formed by vapor deposition or the like on a substrate and utilizes interference that occurs inside thereof for transmitting or reflecting light of only a specific wavelength band. In general, an interference filter is composed of multi-layered dielectric films (for example, $SiO_2$, SiN, or $TiO_2$). According to the present inventor, it has been discovered that dielectric films to compose an interference filter reflect a light component of wavelengths other than a light component of a wavelength that the interference filter transmits at a relatively high percentage (for example, 80% or more). FIG. 2~FIG. 4 are graphs showing relationships between the wavelength and reflectance of an interference filter obtained through experiments by the present inventor. In the respective graphs, the horizontal axis represents wavelength [nm] of an incident light into the interference filter, and the vertical axis represents reflectance [%] of an incident light.

In FIG. 2, the solid line of the graph represents data from the interference filter 31 (transmission wavelength: 340 nm), the dotted line represents data from the interference filter 32 (transmission wavelength: 415 nm), and an alternate long and short dash line represents data from the interference filter 33 (transmission wavelength: 450 nm). In FIG. 3, the solid line of the graph represents data from the interference filter 34 (transmission wavelength: 510 nm), the dotted line represents data from the interference filter 35 (transmission wavelength: 540 nm), and an alternate long and short dash line represents data from the interference filter 36 (transmission wavelength: 568 nm).

In FIG. 4, the solid line of the graph represents data from the interference filter 37 (transmission wavelength: 600 nm), the dotted line represents data from the interference filter 38 (transmission wavelength: 690 nm), and an alternate long and short dash line represents data from the interference filter 39 (transmission wavelength: 800 nm).

As can be understood from these graphs, the interference filters 31–39 have a relatively high transmittance with respect to a light component of wavelengths other than the light component of the wavelength to be transmitted.

The present embodiment utilizes the above-described feature of the interference filters. Namely, by making a light component reflected by each interference filter into an incident light into an interference filter in the next order, an incident light of a relatively high intensity is made incident into the interference filters positioned in the latter orders, as well.

Operations of the spectroscopic instrument 1 will be described by use of FIG. 1. Light L generated from the light source 3 passes, after section dimensions thereof are defined to an appointed value by the lenses 5 and 7 and aperture 9, through the slit 19 and is made incident into the sample cell S. After being transmitted through the sample cell S, the light L passes through the slit 21 and is made incident into the lens 11. The light L is made into parallel light rays by the lens 11 and is made incident into the spectroscopic portion 13 via the slit 23.

The light L made incident into the spectroscopic portion 13 is first made incident into the incident surface of the interference filter 31 and is split by the interference filter 31 into a light component to be transmitted and a light component R1 to be reflected. The light component to be transmitted is a light component mainly of a wavelength 340 nm and is detected by the photodiode 41.

As described in the foregoing, the interference filters have a feature to reflect most of the light component other than a light component of a wavelength to be transmitted. Therefore, the light component R1 to be reflected by the interference filter 31 contains a light component of wavelengths to be transmitted through the interference filters 32–39 in the latter orders with a high intensity. The transmitted light component R1 is made incident into the incident surface of the interference filter 32 and is split by the interference filter 32 into a light component to be transmitted and a light component R2 to be reflected. The light component transmitted through the interference filter 32 is a light component mainly of a wavelength 415 nm, and this light component is detected by the photodiode 42. For similar reasons to the above description, the reflected light R2 contains a light component of wavelengths to be transmitted through the interference filters 33–39 in the latter order with a high intensity.

Subsequently, similarly, light components transmitted through the interference filters 33–39 are detected by the photodiodes 43–49. Accordingly, light components of nine wavelength types can be detected by the spectroscopic instrument 1. Examples of output values [nA] of the light components detected by the photodiodes 41–49 are shown in Table 2.

TABLE 2

| | Output value [nA] | Output value with a single filter [nA] | Ratio to a single filter [%] | Reference [%] |
|---|---|---|---|---|
| Interference filter 31 (340 nm) | 28.9 | 28.9 | 100 | 50 |
| Interference filter 32 (415 nm) | 164.3 | 249.1 | 66.0 | 25.0 |
| Interference filter 33 (450 nm) | 127.7 | 562.8 | 22.7 | 12.50 |
| Interference filter 34 (510 nm) | 805.6 | 1315.0 | 61.3 | 6.25 |
| Interference filter 35 (540 nm) | 1856.1 | 2156.0 | 86.1 | 3.13 |
| Interference filter 36 (568 nm) | 2055.0 | 2587.0 | 79.4 | 1.56 |
| Interference filter 37 (600 nm) | 1540.0 | 2105.0 | 73.2 | 0.78 |
| Interference filter 38 (690 nm) | 4118.0 | 4774.0 | 86.3 | 0.39 |
| Interference filter 39 (800 nm) | 3492.0 | 4051.0 | 86.2 | 0.20 |

Herein, "output value with a single filter" is an output value from the photodiode when light L made incident into the spectroscopic portion 13 is directly made incident into the respective interference filters 31–39. "Ratio to a single filter [%]" is a percentage of the output value from the respective photodiodes 41–49 when the output value with a single filter is provided as 100%. "Reference" is a ratio [%] to a single filter when a half mirror of a transmittance 50% is used in place of the interference filter.

According to the present embodiment, it can be understood that even the light components transmitted through the interference filters positioned in the latter orders (for example, the interference filters 35–39) have relatively great output values. This is obvious at a glance by a comparison between the "ratio to a single filter" and "reference." In the present embodiment, even the interference filters positioned in the latter orders have relatively great percentages of the "ratio to a single filter." This indicates that intensity of a light component detected by each photodiode is relatively high, therefore, even light components of wavelengths transmitted through the interference filters positioned in the latter orders can be improved in detecting efficiency. On the other hand, the ratio to a single filter when a half mirror is used as shown by the "reference" is exponentially reduced. Consequently, it can be understood that since intensity of the light components transmitted through the interference filters positioned in the latter orders becomes significantly small, the detecting efficiency is considerably deteriorated.

Therefore, according to the present embodiment, since multiple wavelengths can be detected without increasing the amount of light from the light source 3, low power consumption can be realized. In addition, according to the present embodiment, since no special components to increase detecting efficiency are required either, a small-sized and low-cost spectroscopic instrument can be provided.

In addition, according to the present embodiment, an incident light into each interference filter is split into a light component to be reflected and a light component to be transmitted, and the reflected light component is made into an incident light of an interference filter positioned in the next order, whereby light components of nine wavelength types are detected. As such, in the present embodiment, since multiple wavelengths are detected by not mechanically but optically selecting a wavelength, multiple wavelengths can be speedily detected. In addition, since a structure is employed wherein a plurality of interference filters 31–39 are arranged so that the light L from the light source 3 is transmitted in order, multiple wavelengths can be detected with a simple structure.

According to the present embodiment having the above effects, it becomes possible to utilize the spectroscopic instrument for a test of multiple samples and multiple items such as, for example, a blood test.

Figure 5:
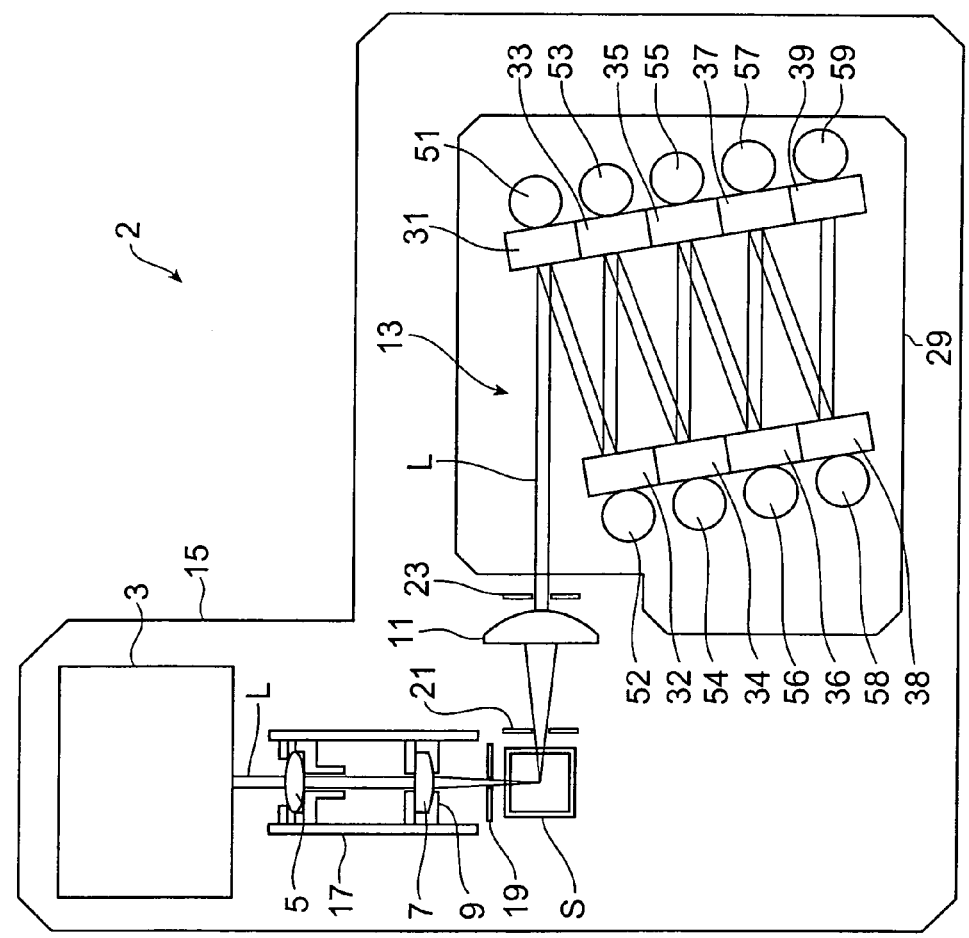
FIG. 5 is a schematic view of a spectroscopic instrument according to the second embodiment of the present invention.

Now, a spectroscopic instrument according to a second embodiment of the present invention will be described. FIG. 5 is a schematic view of a spectroscopic instrument 2 according to the second embodiment. In FIG. 5, identical symbols are used for components equivalent to those of the spectroscopic instrument 1 shown in FIG. 1, whereby description thereof will be omitted.

The spectroscopic instrument 2 detects light components transmitted through the respective interference filters 31–39 by means of photo multipliers 51–59 as photodetecting means examples in place of the photodiodes 41–49. As in the case of light components to compose fluorescence, when the intensity is extremely small, since it is difficult to detect the light components by the photodiodes 41–49, the light components are detected by the photo multipliers 51–59. Herein, the reason why the traveling direction of light L from a light source 3 is changed by 90 degrees at a sample cell S is to prevent the light L from the light source 13 from being directly made incident into a spectroscopic portion 13. Thereby, reliability in detecting respective light components is improved. Herein, the spectroscopic instrument 2 also has similar effects to those of the spectroscopic instrument 1.

According to the spectroscopic instruments 1 and 2, light components of nine wavelength types are detected by providing nine interference filters, which allows light components of different wavelengths to transmit. However, the number of multiple wavelengths detected by a spectroscopic instrument of the present invention is not limited hereto, but the number of multiple wavelengths can be arbitrarily set by changing the number of interference filters to allow light components of different wavelengths to transmit.

In addition, the spectroscopic instruments 1 and 2 cause the lens 11 to make light emitted from the sample cell S into parallel light by a lens 11 and make the same incident into the interference filter, however, when absorption of the interference filter at a specific wavelength is great or when intensity of light emitted from a light source or a sample is small at a specific wavelength, efficient spectroscopy is made possible by focusing on that filter. For example, in the present embodiment, improvement in the detecting light amount is made possible by focusing on the 340 nm interference filter 31, and a difference in the light intensity detected by another interference filter can be made small.

In the spectroscopic instrument according to the present invention, a plurality of interference filters split their respective incident lights into a light component to be reflected and a light component to be transmitted, the reflected light component is made into an incident light into an interference filter positioned in the next order, and light from the light source is transmitted to the plurality of interference filters in order, whereby multiple wavelengths are detected. According to the present inventor, it has been discovered that dielectric layers to compose an interference filter have relatively satisfactory features to reflect a light component of wavelengths other than a light component of a wavelength transmitted through the interference filter. Accordingly, an incident light of a relatively high intensity is made into interference filters positioned in the latter order as well, and multiple wavelengths can be detected at a high detecting efficiency.

In addition, according to the spectroscopic instrument according to the present invention, an incident light into the respective interference filters are split into a light component to be transmitted and a light component to be reflected, and the reflected light component is made into an incident light into an interference filter positioned in the next order, therefore, speedy detection of multiple wavelengths becomes possible.

According to a spectroscopic method of the present invention, it becomes possible to detect multiple wavelengths at a high detecting frequency and at a high speed.

Moreover, the spectroscopic instrument according to the aforementioned embodiment comprises a plurality of photodetectors arranged so that the above-described light is made incident in time series at the speed of light, and the above-described photodetectors each have a photoelectric transducer and an interference filter fixed to the light incident side of the photoelectric transducer, a transmitting wavelength and a reflecting wavelength band of the respective interference filters are different, and a transmitting wavelength of the interference filter of a latter order is included in a reflecting wavelength band of the interference filter of a former order.

Herein, irrespective of the transmitting wavelength of the interference filter, a total reflection mirror having an aperture may be provided on the light incident surface side thereof.

In addition, if the plurality of photodetectors are arranged in a circle, an air flow-in path into the inside of the circle becomes narrow, therefore, an output fluctuation of the photodetectors caused by air undulations can be suppressed.

In addition, if an infrared cut filter is arranged on the near side of the photodetectors, generation of noise caused by infrared light can be suppressed, and if the inner surface of a cylindrical body to compose a photodetector is black, noise caused by an internal reflection of the cylindrical body can be suppressed.

Hereinafter, description will be given in detail.

Figure 6:
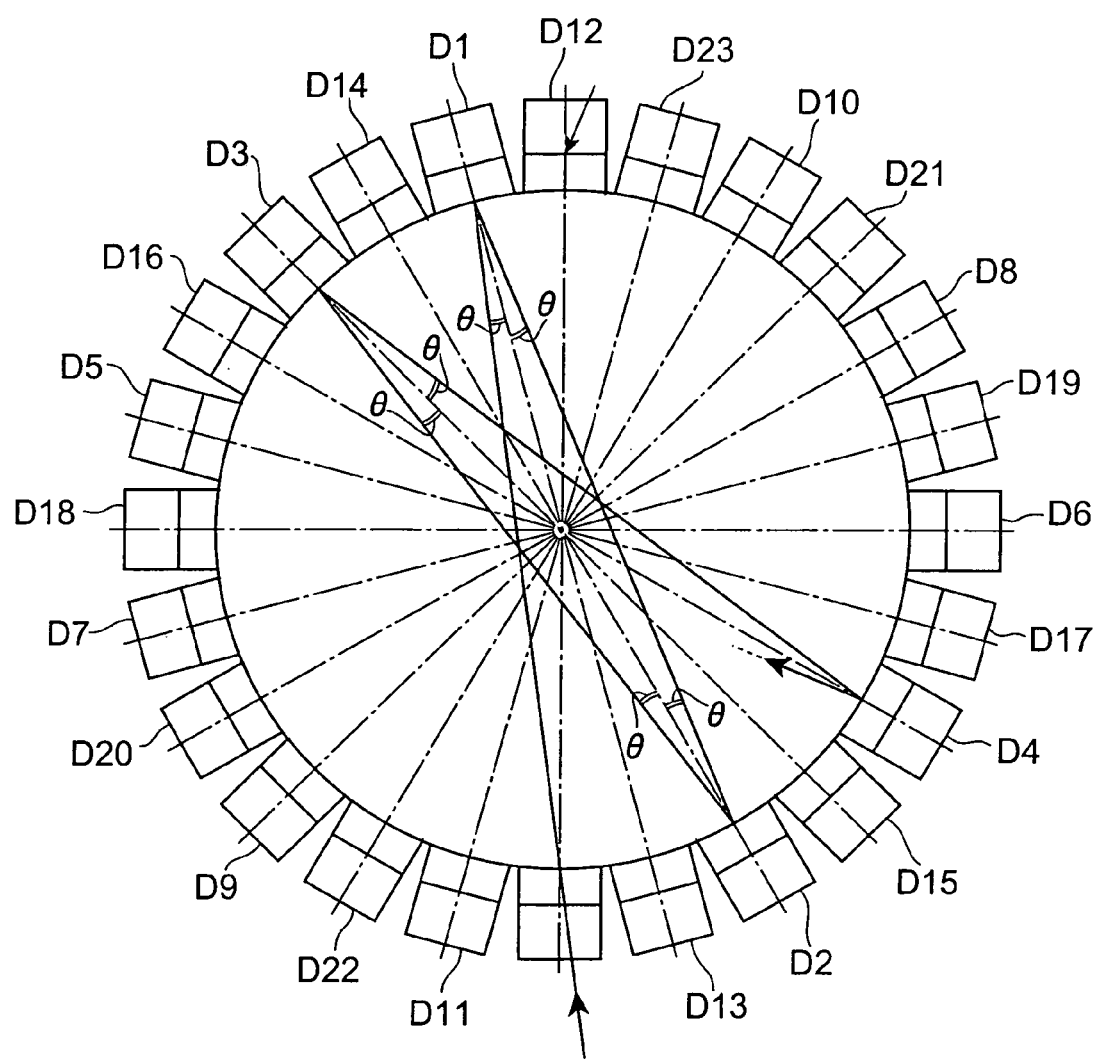
FIG. 6 is a plan view of a spectroscopic instrument according to another embodiment.

FIG. 6 is a plan view of a spectroscopic instrument according to another embodiment. This spectroscopic instrument comprises, similar to the aforementioned spectroscopic instrument, a plurality of photodetectors D1–D22. Herein, focusing on the first-order photodetector D1, this is referred to as a first photodetector, and the next-order photodetector D2 is referred to as a second photodetector. Since components of the plurality of photodetectors D1–D22 are identical except for interference filter characteristics, herein, a description will be given of the photodetector D1 as a representative.

Figure 7:
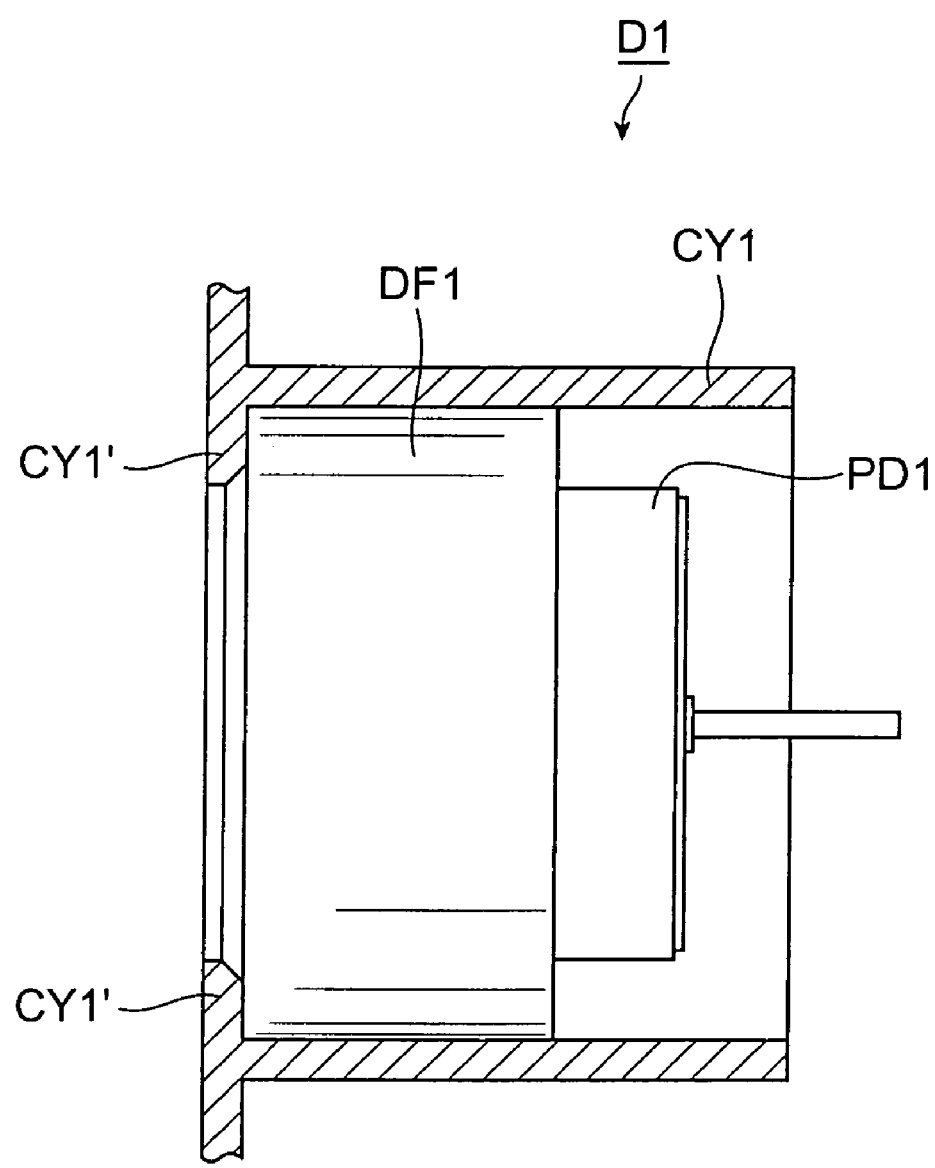
FIG. 7 is a sectional view of a first photodetector D1 when a first photodetector D1 is cut along the optical axis of the first photodetector D1.

FIG. 7 is a sectional view of a first photodetector D1 when the first photodetector D1 is cut along the optical axis of the first photodetector D1.

The photodetector D1 has a first photodiode (a first photoelectric transducer) PD1 and a first interference filter DF1 fixed to the light incident side of the first photodiode PD1. The first interference filter DF1 has a disk shape, and its side circumferential surface is in contact against the inner surface of a cylindrical body CY1 and is fitted in the inside of this cylindrical body CY1, and the cylindrical body CY forms a holder. Namely, the first cylindrical body CY1 accommodates the first photodiode PD1 and has an opening, and the opening of the first cylindrical body CY1 is blocked by the first interference filter PD1.

The light incident surface side of the cylindrical body CY1 is bent inward, and against this bent portion CY', the circumference of the light incident surface of the first interference filter DF1 is in contact, whereby the first interference filter DF1 is positioned in the optical axis direction. To the light emitting surface of the first interference filter DF1, the first photodiode PD1 is attached. The cylindrical body CY1 accommodates the first interference filter DF1 and first photodiode PD1, wherein its inner surface has received a non-reflective treatment. Namely, the inner surface of the cylindrical body CY1 has been painted black. Namely, the color of the inner wall of the cylindrical body CY1 is black, thereby unnecessary reflection is suppressed to carry out accurate detection.

Herein, an n-th order photodetector is a conversion of the first photodetector D1 into an n-th photodetector, and in a case of the second photodetector D2, this second photodetector D2 has a second photodiode (second photoelectric transducer (PD2)) and a second interference filter (DF2) fixed to the light incident side of the second photodiode (PD2).

Now, FIG. 6 will be referred to again.

The second photodetector D2 is arranged so that a reflected light from the first interference filter DF1 is made incident, and a transmitting wavelength ($\lambda_{T1}$) of the first interference filter DF1 is different from a reflecting wavelength band ($\Delta\lambda_{R1}$) of the same, and a transmitting wavelength ($\lambda_{T2}$) of the second interference filter (DF2) is included in the reflecting wavelength band ($\Delta\lambda_{R1}$) of the first interference filter DF1.

The third photodetector D3 is arranged so that a reflected light from the second interference filter (DF2) is made incident, and has a third photodiode (PD3) and a third interference filter (DF3) fixed to the light incident side of the third photodiode (PD3). A transmitting wavelength ($\lambda_{T2}$) of the second interference filter (DF2) is different from a reflecting wavelength band ($\Delta\lambda_{R2}$) of the same, and a transmitting wavelength ($\lambda_{T3}$) of the third interference filter (DF3) is included in the reflecting wavelength band ($\Delta\lambda_{R2}$) of the second interference filter.

By use of "n", which is an integer equal to 1 or more, this relationship can be expressed as follows. Namely, an n+1-th photodetector (Dn+1) is arranged so that a reflected light from an n-th interference filter (DFn) is made incident, and a transmitting wavelength ($\lambda_{Tn}$) of the n-th interference filter (DFn) is different from a reflecting wavelength band ($\Delta\lambda_{Rn}$) of the same, and a transmitting wavelength ($\lambda_{Tn+1}$) of the n+1-th interference filter (DFn+1) is included in the reflecting wavelength band ($\Delta\lambda_{Rn}$) of the n-th interference filter (DFn).

A light made incident into a spectroscopic instrument is made incident with an incident angle $\theta$ into the photodetector D1, a light reflected by the photodetector D1 is made incident with an incident angle $\theta$ into the next-order photodetector D2, and a light reflected by the photodetector D2 is further made incident with an incident angle $\theta$ into the next-order photodetector D3. Namely, the incident angle $\theta$ of light into the first interference filter is greater than 0° and not more than 10°, and the incident angle $\theta$ of the light into the second interference filter (DF2) is greater than 0° and not more than 10°. In the present example, $\theta=7.50°$. This is because, if the incident angle $\theta$ exceeds 10°, transmittance of a wavelength made incident into the interference filter is deteriorated and a wavelength shift occurs.

Focusing on the first, second, and third photodetectors D1, D2, and D3, the first, second, and third photodetectors D1, D2, and D3 are arranged so that normal lines to the light incident surfaces of the first, second, and third interference filters DF1, (DF2), and (DF3) intersect at one point Q. By arranging the respective photodetectors as such, the photodetectors gradually form a circle, and the circular internal space is gradually closed to the outside, therefore, influences of dust and undulations of outside air can be suppressed to carry out accurate detection.

Namely, this spectroscopic instrument comprises a plurality of photodetectors Dn (n is an integer equal to 1 or more) arranged so that a light is made incident in time series at the speed of light, and the photodetectors Dn each have a photodiode PDn and an interference filter DFn fixed to the light incident side of the photodiode PDn, a transmitting wavelength $\lambda_{Tn}$ and a reflecting wavelength band $\Delta\lambda_{Rn}$ of each interference filters DFn are different, and a transmitting wavelength $\lambda_{Tn+1}$ of a latter-order interference filter DFn+1 is included in a reflecting wavelength band $\Delta\lambda_{Rn}$ of the former-order interference filter DFn, Moreover, these photodetectors D1–D23 are arranged in a circular shape, and accurate detection can be carried out. Herein, in order to form a circle, the photodetectors D1–D23 are arranged so that normal lines to the light incident surfaces of the respective photodetectors D1–D23 pass through one point. Although 23 photodetectors have been arranged in the present example, as a matter of course, this quantity is appropriately determined according to the number of wavelengths for which spectroscopy is demanded. In addition, when the quantity of photodetectors is small, shading materials are arranged in place of photodetectors.

In the present example, although the photodetectors D1–D23 have been made identical except for the interference filter construction, a total reflection mirror having an aperture may be provided on the light incident surface side of the interference filter. Although all photodetectors D1–D23 may be replaced by such mirror-type photodetectors, for example, only the photodetectors D15–D23 on the latter-order side where light intensity becomes relatively weak may be replaced by total reflection mirror-type photodetectors. Herein, a description will be given on the premise that, as a representative photodetector, the first photodetector D1 is a total reflection mirror-type photodetector.

Figure 8:
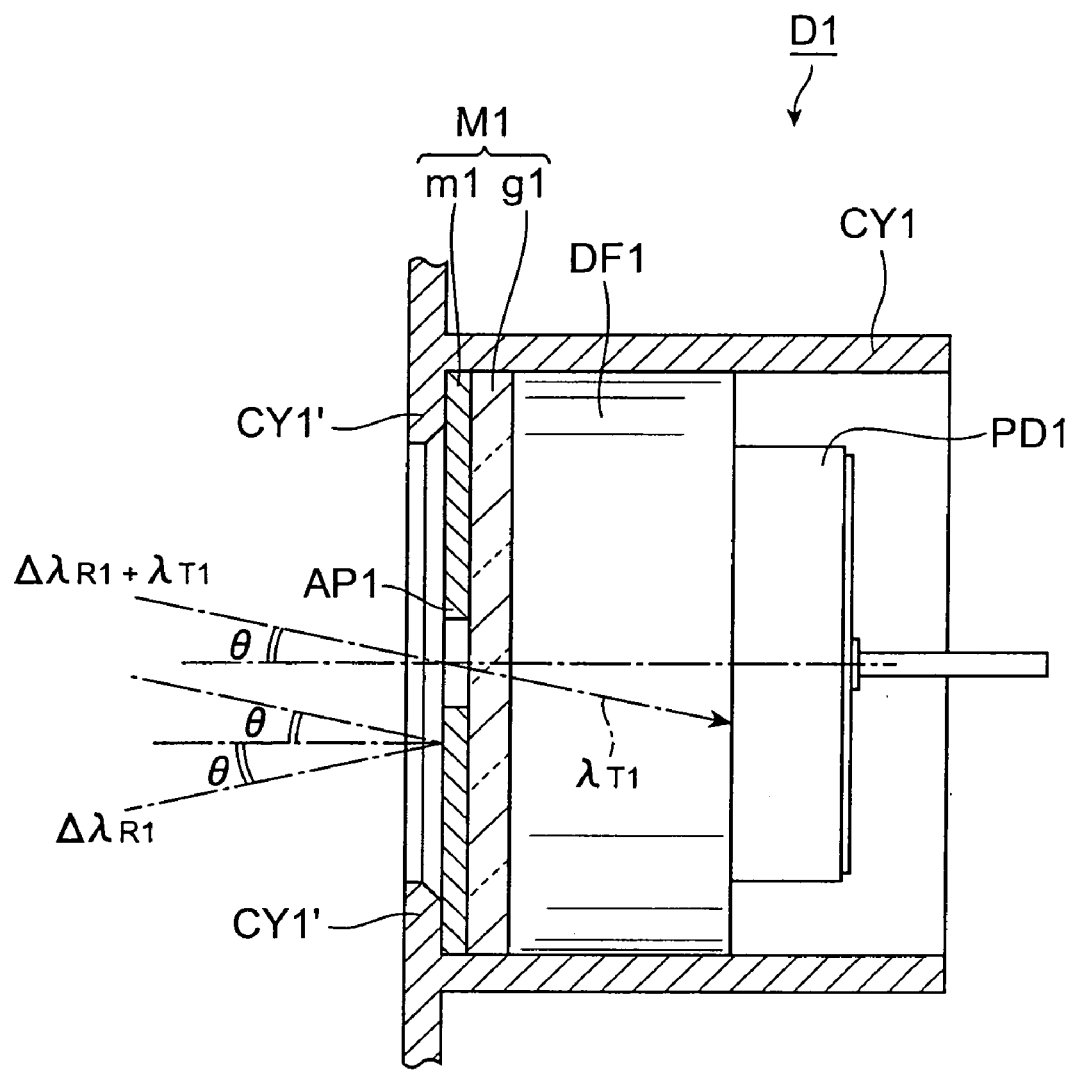
FIG. 8 is a sectional view of a first photodetector D1 when a total reflection mirror-type first photodetector D1 is cut along the optical axis of the first photodetector D1.

FIG. 8 is a sectional view of a first photodetector D1 when a total reflection mirror-type first photodetector D1 is cut along the optical axis of the first photodetector D1.

Figure 9:
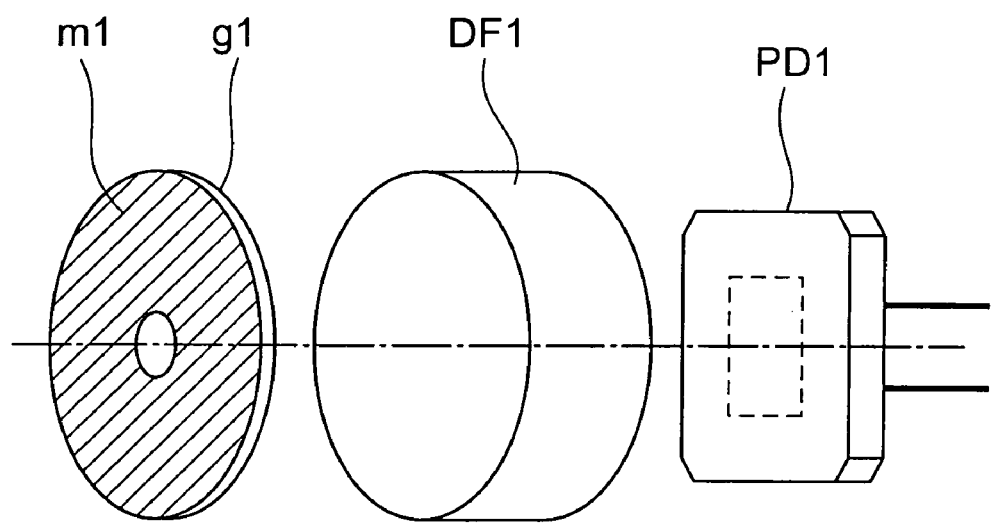
FIG. 9 is a view of a photodetector D1 showing internal components of a photodetector D1 in an exploded manner.

FIG. 9 is a view of a photodetector D1 showing internal components of a photodetector D1 in an exploded manner.

The difference from the photodetector D1 shown in FIG. 6 is in that a total reflection mirror M1 is provided on the light incident surface side of the interference filter DF1 and a holder bent portion CY' is in contact against the outer circumferential portion of the light incident surface of the total reflection mirror M1. Other aspects of the construction are identical to those shown in FIG. 6.

Namely, in this spectroscopic instrument, to the light incident surface of the first interference filter DF1, attached is a total reflection mirror M1 having an aperture AP1.

The total reflection mirror M1 is composed of a glass plate g1 and a metal reflecting film m1 formed on the glass plate g1. The metal reflecting film m1 is made of aluminum and has an aperture AP1 for a light incidence. Although the metal reflecting film m1 can be formed on the glass plate g1 by a vapor deposition method, it may also be formed by a wet plating method. The glass plate g1 is formed on the light incident surface of the interference filter DF1.

A specific wavelength component $\lambda_{T1}$ of light made incident into the aperture AP1 of the metal reflecting film m1 is transmitted through the glass plate g and interference filter DF1 and reaches the light incident surface of the photodiode PD1, that is, a photodetecting region. In the photodetecting region, a photoelectric conversion is carried out and an electric signal of a signal intensity according to the incident light intensity is outputted from the photodiode PD1.

A wavelength band $\Delta\lambda_{R1}$ of light incident onto the metal reflecting film m1 is reflected and reaches the following-order photodetector D2.

Namely, the present spectroscopic instrument comprises a plurality of photodetectors D1–D23 arranged so that a light is made incident in time series at the speed of light, and when a description is given of the photodetector D1 as are presentative of the photodetectors D1–D23 (D15–D23), this photodetector D1 has a photodiode PD1, an interference filter DF1 fixed to the light incident side of the photodiode PD1, and a total reflection mirror M1 having an aperture AP1 fixed to the light incident side of the interference filter DF1.

In this case, a light having an intensity of an order that the photodetector D1 can detect passes through the inside of the aperture AP1, and by effectively reflecting the remaining light by the total reflection mirror M1, a deterioration in detection sensitivity can be suppressed in the latter-order detectors.

Such a total reflection mirror-type photodetector D1 can also be applied to the spectroscopic instrument as shown in FIG. 1, as well.

Figure 10:
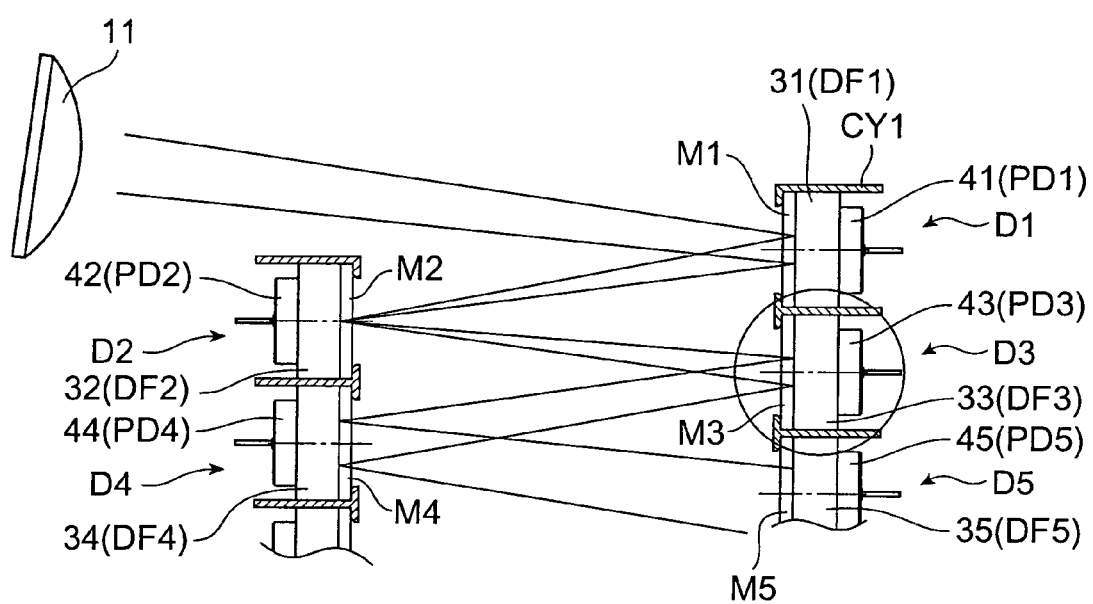
FIG. 10 is a view showing an example where, in the spectroscopic instrument shown in FIG. 1, total-reflection mirror-type photodetectors D1–D5 . . . have been applied.

FIG. 10 is a view showing an example where, in the spectroscopic instrument shown in FIG. 1, total reflection mirror-type photodetectors D1–D5 . . . have been applied. The photodetectors D1, D3, D5 . . . of the odd-numbered orders are lined up in a row to form a first photodetector array, the photodetectors D2, D4, . . . of the even-numbered orders are lined up in a row to form a second photodetector array. The first and second photodetector arrays are opposed to each other. In the present example, a position of conversion by the lens 11 has been set on the second photodetector D2, the light becomes more divergent as the position shifts toward the latter-order side beyond the position of conversion. This light can be made into a parallel light so that divergence hardly occurs. The aforementioned aperture diameter may be enlarged on the latter-order side beyond the position of conversion to meet light divergence. Moreover, the aperture diameters can be identical.

Figure 11:
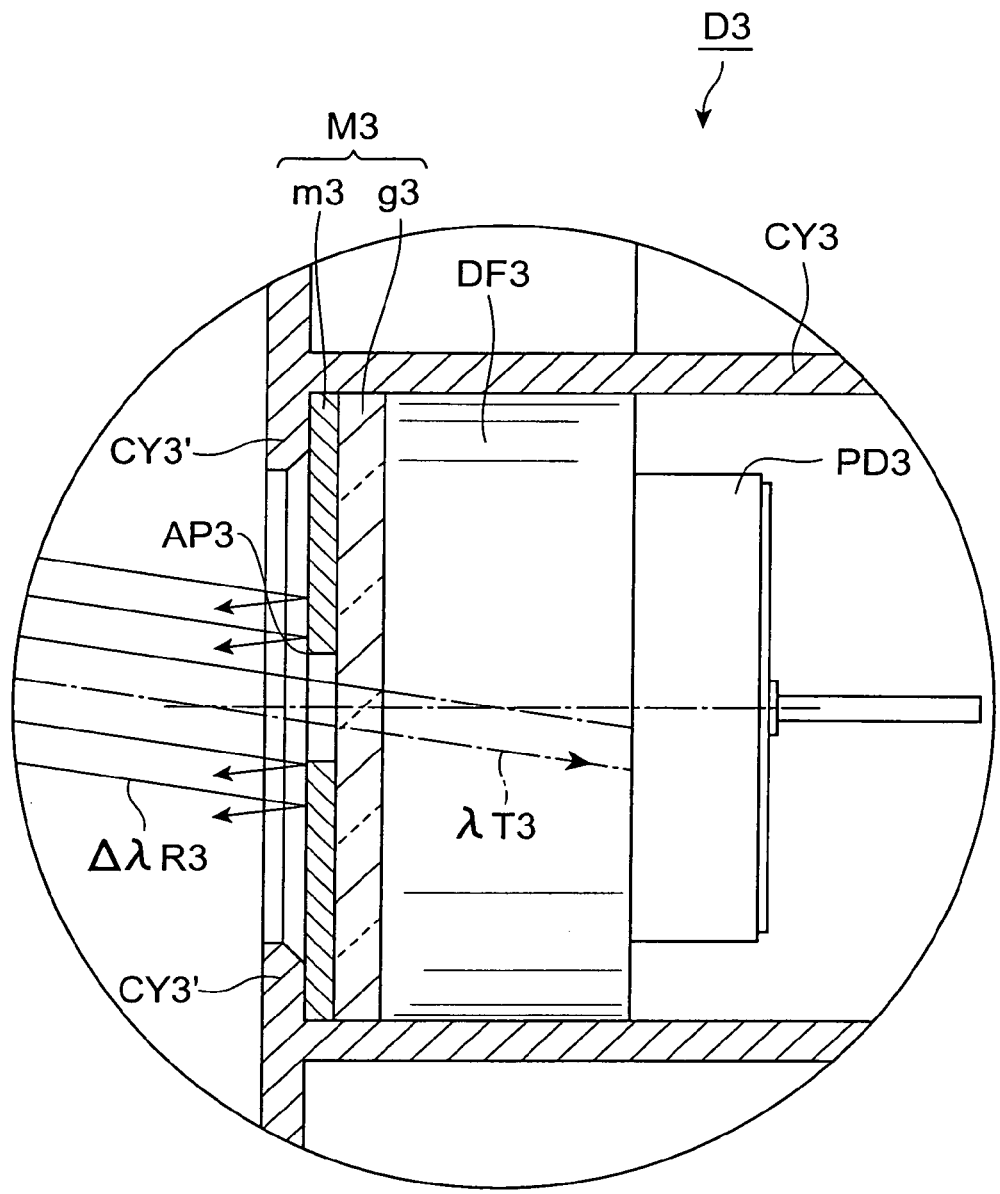
FIG. 11 is an enlarged sectional view of the third photodetector D3 shown in FIG. 10.

FIG. 11 is an enlarged sectional view of the third photodetector D3 shown in FIG. 10. Although the structure of the third detector D3 is identical to that of the first detector D1 except for characteristics of the interference filter DF3, the third detector D3 comprises, in order from the light incident side, a total reflection mirror M3 composed of a metal reflecting film m3 and a glass plate g3, a third interference filter DF3, and a photodiode PD3, and these are accommodated in a cylindrical body CY3. The front end portion of the cylindrical body CY3 is bent inward, and the inner surface of the bent portion CY3' is in contact against the outer circumferential portion of the total reflection mirror M3. A wavelength component $\lambda_{T3}$ of light transmitted through an aperture AP3 of the total reflection mirror M3 reaches the photodiode PD3, and a wavelength band $\Delta\lambda_{R3}$ of light incident onto the metal reflecting film m3 is reflected.

Figure 12:
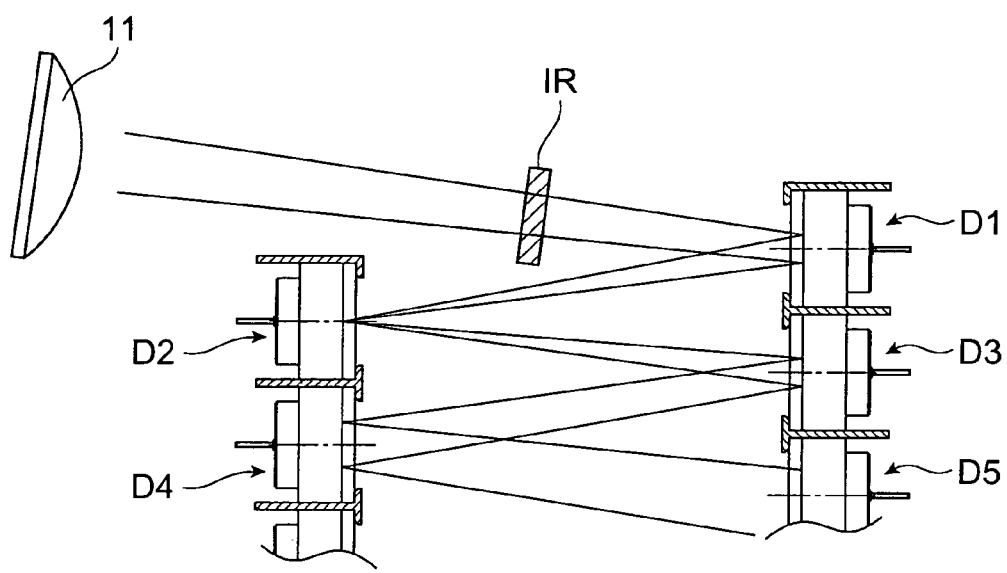
FIG. 12 is a view showing an example where, in the spectroscopic instrument shown in FIG. 1, an infrared cut filter is applied.

Herein, as shown in FIG. 12, the spectroscopic instrument may further comprise an infrared cut filter arranged on the path of an incident light into the first interference filter DF1.

Thereby, depending on the interference filter, even if it has a characteristic to transmit an infrared-region wavelength, detection of this component as noise can be prevented.

Figure 13:
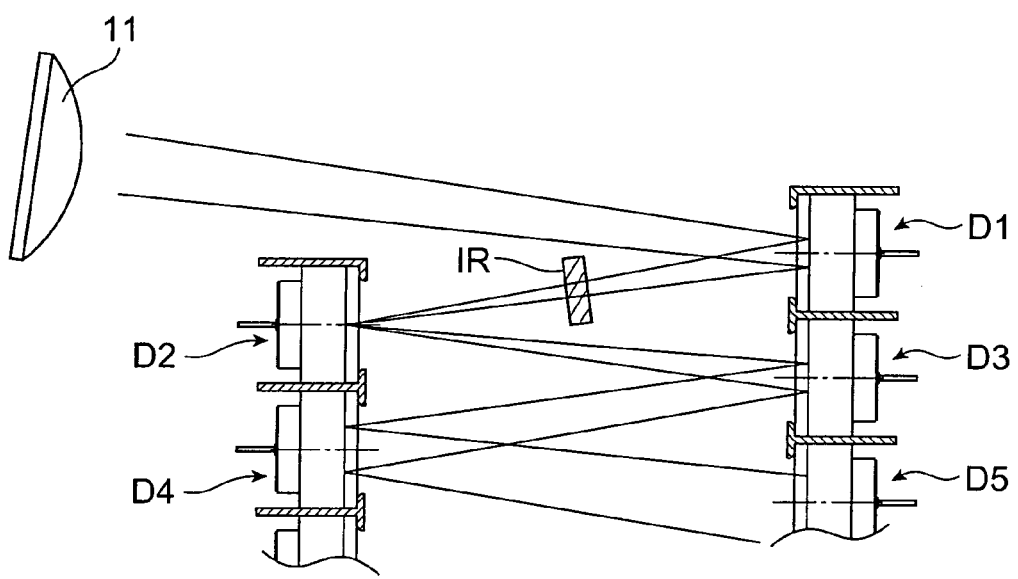
FIG. 13 is a view showing an example where, in the spectroscopic instrument shown in FIG. 1, an infrared cut filter is applied.

Moreover, as shown in FIG. 13, the spectroscopic instrument may further comprise an infrared cut filter arranged on the path of an incident light into the second interference filter DF2.

Moreover, although the aforementioned photoelectric transducer PDn was a photodiode, this may be a photo multiplier.

Industrial Applicability

The present invention can be utilized for a spectroscopic instrument and a spectroscopic method used in a blood test, for example.

The invention claimed is:

1. A spectroscopic instrument for detecting a plurality of light components different in wavelengths, comprising:
a plurality of interference filters which are respectively different in wavelengths of light components to be transmitted therethrough and to which a light from a light source is transmitted in order and
a plurality of photodetecting means corresponding to each of said plurality of interference filters, for detecting a light component transmitted through the corresponding interference filter, wherein
each of said plurality of interference filters splits an incident light into a light component to be reflected and a light component to be transmitted and makes the reflected light component into an incident light into an interference filter positioned in the next order, whereby the light from said light source is transmitted to said plurality of interference filters in order,
an incident angle of light into each of said interference filters is greater than 0° and not more than 10°.

2. A spectroscopic method for detecting a plurality of light components different in wavelengths, in which:
at each of a plurality of interference filters respectively different in wavelengths of light components to be transmitted therethrough, an incident light into each interference filter is split into a light component to be reflected and a light component to be transmitted and the reflected light component is made into an incident light into an interference filter positioned in the next order, whereby a light from a light source is transmitted to said plurality of interference filters in order so as to detect light components transmitted through the respective interference filters,
an incident angle of light into each of said interference filters is greater than 0° and not more than 10°.

3. A spectroscopic instrument comprising:
a first photodetector having a first photoelectric transducer and a first interference filter fixed to the light incident side of said first photoelectric transducer and
a second photodetector arranged so that a reflected light from said first interference filter is made incident, having a second photoelectric transducer and a second interference filter fixed to the light incident side of said second photoelectric transducer, wherein
a transmitting wavelength of said first interference filter is different from a reflecting wavelength band of the same, and a transmitting wavelength of said second interference filter is included in the reflecting wavelength band of said first interference filter, an incident angle of light into said first interference filter is greater than 0° and not more than 10°, and an incident angle of light into said second interference filter is greater than 0° and not more than 10°.

4. The spectroscopic instrument as set forth in claim 3, further comprising: a third photodetector arranged so that a reflected light from said second interference filter is made incident, having a third photoelectric transducer and a third interference filter fixed to the light incident side of said third photoelectric transducer, wherein
a transmitting wavelength of said second interference filter is different from a reflecting wavelength band of the same, and a transmitting wavelength of said third interference filter is included in the reflecting wavelength band of said second interference filter.

5. The spectroscopic instrument as set forth in claim 4, wherein
said first, second, and third photodetectors are arranged so that normal lines to the light incident surfaces of said first, second, and third interference filters intersect at one point.

6. The spectroscopic instrument as set forth in claim 3, further comprising: an infrared cut filter arranged on the path of an incident light into said first interference filter.

7. A spectroscopic instrument comprising:
a first photodetector having a first photoelectric transducer and a first interference filter fixed to the light incident side of said first photoelectric transducer and
a second photodetector arranged so that a reflected light from said first interference filter is made incident, having a second photoelectric transducer and a second interference filter fixed to the light incident side of said second photoelectric transducer, wherein
a transmitting wavelength of said first interference filter is different from a reflecting wavelength band of the same, and a transmitting wavelength of said second interference filter is included in the reflecting wavelength band of said first interference filter, wherein
a total reflection mirror having an aperture is attached to the light incident surface of said first interference filter.

8. The spectroscopic instrument as set forth in claim 3, comprising: a first cylindrical body which accommodates said first photoelectric transducer and has an opening, wherein
the opening of the first cylindrical body is blocked by said first interference filter.

9. The spectroscopic instrument as set forth in claim 8, wherein
the color of the inner wall of said first cylindrical body is black.

10. A spectroscopic instrument comprising: a plurality of photodetectors arranged so that said light is made incident in time series at the speed of light, wherein
said photodetectors each have a photoelectric transducer and an interference filter fixed to the light incident side of the photoelectric transducer,
a transmitting wavelength and a reflecting wavelength band of the respective interference filters are different, and a transmitting wavelength of said interference filter of a latter order is included in a reflecting wavelength band of said interference filter of a former order,
an incident angle of light into said first interference filter is greater than 0° and not more than 10°, and an incident angle of light into said second interference filter is greater than 0° and not more than 10°.

11. The spectroscopic instrument as set forth in claim 10, wherein
said plurality of photodetectors are arranged in a circular shape.

12. The spectroscopic instrument as set forth in claim 11, wherein
said photodetectors are arranged so that normal lines to the light incident surfaces of said respective photodetectors pass through one point.

13. A spectroscopic instrument comprising: a plurality of photodetectors arranged so that said light is made incident in time series at the speed of light, wherein
said photodetectors each have a photoelectric transducer, an interference filter fixed to the light incident side of said photoelectric transducer, and a total reflection mirror having an aperture fixed to the light incident side of said interference filter.

14. The spectroscopic instrument as set forth in any one of claims 3 through 13, wherein
said photoelectric transducer is a photodiode or a photo multiplier.

15. The spectroscopic instrument as set forth in any one of claims 1 through 13, further comprising holders, each of said holders accommodating each of said interference filters and each of said photoelectric transducers.

16. The spectroscopic instrument as set forth in any one of claims 1 through 13, further comprising a holding portion, said holding portion holding all of said interference filters.

17. The spectroscopic instrument as set forth in any one of claims 1 through 13, further comprising a casing for accommodating all of said photodetectors.

18. The spectroscopic instruction as set forth in any one of claims 1 through 13, further comprising a lens for entering light to one of said interference filters, said lens focusing light on this interference filter.

* * * * *